United States Patent [19]

James et al.

[11] Patent Number: 5,539,482

[45] Date of Patent: Jul. 23, 1996

[54] GLAUCOMA TESTING USING NON-LINEAR SYSTEMS IDENTIFICATION TECHNIQUES

[75] Inventors: Andrew C. James, Reid; Teddy L. Maddess, Kaleen, both of Australia

[73] Assignee: The Australian National University, Australian Captial Territory, Australia

[21] Appl. No.: 25,423

[22] Filed: Mar. 1, 1993

[30] Foreign Application Priority Data

Feb. 28, 1992 [AU] Australia .................................. PL1161

[51] Int. Cl.⁶ ................................ A61B 3/10; A61B 5/04
[52] U.S. Cl. ........................ 351/246; 351/205; 351/221; 128/745
[58] Field of Search .................... 128/639, 745; 606/4, 6; 351/205, 211, 221, 224, 237, 246, 209

[56] References Cited

U.S. PATENT DOCUMENTS

| | | | |
|---|---|---|---|
| 4,634,243 | 1/1987 | Massof et al. .......................... | 351/243 |
| 4,822,162 | 4/1989 | Richardson et al. ................. | 351/246 X |
| 5,065,767 | 11/1991 | Maddess ................................ | 128/745 |
| 5,176,147 | 1/1993 | Bodis-Wollner ....................... | 128/745 |
| 5,233,373 | 8/1993 | Peters et al. .......................... | 128/745 X |

*Primary Examiner*—William L. Sikes
*Assistant Examiner*—David R. Parsons
*Attorney, Agent, or Firm*—Mion, Zinn, Macpeak & Seas Sughrue

[57] ABSTRACT

A diagnostic test for glaucoma, which can detect the early stages of this disease, uses a pattern electroretinogram of a subject to assess any reduction of the density of $M_y$ ganglion cells in a part of the subject's retina. The visual field of the eye of the subject is divided into a number of zones, and a respective visual stimulus signal is applied to each zone. The visual stimulus signals are generated in accordance with data obtained from determinations of the critical spatial frequency (Nyquist frequency) of persons with normal vision, obtained from observations of the "aliasing" phenomenon. Typical visual stimulus signals are grating patterns, with the contrast of the signal applied to each zone modulated with a different temporal frequency in the range of from 10 Hz to 45 Hz. Any differences between the electroretinogram response component for an individual zone and the expected response component for that zone indicates a change in the $M_y$ ganglion cell function in that zone, attributable to the effect of glaucoma.

8 Claims, 6 Drawing Sheets

FIG. 3

NORMAL SUBJECT, FOURIER TRANSFORM

FIG. 4

NORMAL SUBJECT, ARGAND DIAGRAM OF FOURIER COEFF.

o - SECOND HARMONICS
* - OFF-DIAGONAL SUM FREQUENCIES
+ - NOISE FREQUENCIES
DASHED LINE, 95% SIGNIFICANCE

RELATIVE SENSITIVITY, %. SIGNIFICANT ABOVE 55%

FIG. 9

GLAUCOMA TESTING USING NON-LINEAR SYSTEMS IDENTIFICATION TECHNIQUES

TECHNICAL FIELD

This invention concerns the detection of damage to the retina of the human eye by the disease glaucoma. More particularly, it concerns a method and apparatus whereby a person suffering from glaucoma can be diagnosed rapidly and objectively while the disease is in its early stages, thus improving the prospects for successful treatment to reduce the progress of the disease and prevent the irreversible blindness that is a characteristic of glaucoma.

BACKGROUND TO THE INVENTION

In the human eye, the final stage of image processing in the retina is performed by retinal ganglion cells. The axons of the ganglion cells project out of the eye to form the optic nerve. Glaucoma, which produces irreversible blindness if not treated early enough, destroys these ganglion Cells. A typical "early" sign of glaucoma is the loss of a portion of the peripheral visual field, referred to as "scotoma". Unfortunately, by the time a scotoma is detected, the disease has reached a stage where treatment can at best prevent further irreversible blindness.

A symptom of glaucoma is an increase in the patient's intraocular tension. Thus one approach that is used to screen patients for glaucoma at an earlier stage than when a scotoma has developed is to test the intraocular tension of a patient. The measurement of intraocular tension, however, usually involves the use of drugs, is time consuming, and is unpleasant for the patient.

Moreover, some glaucoma patients do not exhibit intraocular tensions above about 21 mm of mercury (such patients have what is called "normal-tension glaucoma"). Thus, testing the intraocular tension of a person is not a reliable method for the early detection of glaucoma.

Another proposal for the early detection of glaucoma has involved the assessment of colour vision defects. Simple tests of colour vision defects, however, have shown a lack of correlation between the defects noted and the presence of optic disc cupping. More complex tests of colour vision defects, which involve anomaloscopy, ere too difficult for clinical use. Moreover, those tests cannot differentiate between colour vision defects caused by glaucoma and colour deficits resulting from amblyopia and optic neuritis. In addition, it has been reported that up to 25 per cent of patients who have glaucomatous scotoma exhibit no colour deficit. Thus assessment of colour deficits in a person's vision is not a reliable method of detecting glaucoma in its early stages, even if it should become practical to perform detailed colour vision tests clinically.

Another conventional method for determining whether an eye has been damaged by glaucoma involves the use of perimetry. In a typical perimetric investigation, a patient is presented with a series of small luminous dots projected onto a screen which has been placed in front of the patient. The patient's vision is assessed on the basis of whether the patient testifies to seeing each dot as it is presented. This procedure, being a serial search, is very time consuming and is prone to errors arising from subjects' fallibility. Moreover, this technique is not primarily designed for assessing glaucomatous damage but rather for assessing localised blind spots, which can arise from a variety of retinal and central nervous system disorders that affect vision. In particular, perimetric investigations take no account of the spatial scale of the visual system, for they typically use the same size dots in all parts of the visual field, and thus they do not investigate whether any particular visual subsystem has been damaged by glaucoma.

DISCLOSURE OF THE PRESENT INVENTION

The prime object of the present invention is the provision of a rapid and reliable test for glaucoma which is specific to this disease and which is effective at the early stages of glaucoma. A secondary object of the present invention is the provision of a reliable test for glaucoma which permits the parallel assessment of multiple parts of the visual field of a subject at the same time with multiple stimuli presented simultaneously to different parts of the visual field, thus avoiding the need for a series of stimuli to be tested to build up a map of deficits to the visual field.

To achieve the prime objective, the present invention utilises electroretinogram measurements during the observation, by a subject, of stimuli having a spatial distribution and a spatio-temporal structure that are tailored to a visual subsystem which is highly likely to indicate the presence of damage due to glaucoma. In particular, the present invention uses special visual stimuli, presented to different portions or "zones" of the visual field, in pattern electroretinogram measurements. The special visual stimuli are established using data obtained from observations of a geometric interference phenomenon, known as "aliasing", that is believed to be affected by the number of large ganglion cells present in the retina, to provide an indication of the areal density of $M_y$ cells on the retina of the subject. This data or information is the used to set the spatial scale of the patterns presented to each zone of the visual field and also to each part of the retina of the eye, in a novel pattern electroretinogram (PERG) measurement.

Thus the responses obtained to the simultaneously presented PERG patterns are particularly suited to assess the presence of damage to the retinal ganglion cells in each part of the retina onto which the simultaneously presented PERG patterns project.

According to the present invention, there is provided a method of assessing the presence of glaucomatous damage to the visual system of a subject, the method comprising the steps of:

(a) dividing the visual field of view of the subject into a number of zones;

(b) generating, using data about the areal density of retinal ganglion cells on the retina of the human eye, such data being obtained from determinations of the critical spatial frequency (Nyquist frequency) of persons with normal vision, a set of visual stimuli signals which, on the basis of the measured areal density of receptors, should elicit an electroretinogram response signal from the subject;

(c) applying each of the visual stimuli signals to a respective one of the zones of the field of view of the eye of the subject, and obtaining a pattern electroretinogram response signal which can be decomposed into components, each component relating to a respective one of the zones; and (d) comparing the electroretinogram response amplitudes and phases for the zones and the expected response components for the zones, and noting any significant difference between the observed and the expected response amplitude and phase of any zone of the visual field, any such difference indicating a change in the $M_y$ cell function in that zone, which is attributable to the effect of glaucoma on the subject.

Preferably the application of the visual stimuli signals to the zones of the visual field is effected simultaneously, and the responses to the stimuli signals are measured simultaneously using a single electrode mounted on the cornea or sclera of the subject.

It is also preferred that the application of the visual stimuli is such that the visual stimulus signal applied to one zone of the visual field is orthogonal to the visual stimulus signal that is applied to the adjacent zone or zones. In this case the stimuli are orthogonal in the sense that the inner product between any two of the functions describing the time varying contrast in each region is equal to zero. Such orthogonal stimuli signal application can conveniently be effected by modulating the contrast of each region with a different temporal frequency in the range of from 10 Hz to 45 Hz, preferably in the range of from 22 Hz to 24 Hz.

It is also preferred that the strength of the response signals is measured (examined) at the second harmonic of each stimulus frequency, since the the spatial frequency doubled illusion is a frequency doubled temporal response.

The spatial frequencies used in feature (b) of this invention were determined by the mean eccentricity of each zone, and represent half the value of the critical spatial frequency predicted for each such eccentricity.

The reasoning which led to the development of the present invention is provided below.

It has been known for many years that psycho-physical phenomena are observed by a subject with normal vision who is presented with particular optical patterns. For example, in 1966, D H Kelly reported, in his paper entitled "Frequency doubling in visual responses" (which was published in the *Journal of the Optical Society of America*, Volume 56, page 1628, 1966), that when sinusoidal grating patterns with spatial frequencies below a few cycles per degree are modulated so that the contrast between the bars or striations of the pattern is varied at rates higher than 10 Hz, the grating patterns appear as spatial frequency-doubled sinusoids to persons of normal vision. D H Kelly's subsequent work (reported in his paper entitled "Nonlinear visual responses to flickering sinusoidal gratings", which was published in the *Journal of the Optical Society of America*, Volume 71, page 1051, 1981) has shown that this second-harmonic distortion of the human visual response is due to the optical pathway between the eye and the brain having both a linear component and a non-linear component.

It is also known that the retinal ganglion cells of higher primates, including humans, are of two types, namely "M" type ganglion cells and "P" type ganglion cells, each of which respond to visual stimuli. However, the P type ganglion cells respond in a sluggish manner and do not contribute to the production of the images with which the present invention is concerned. The M type ganglion cells consist of "y-type" ganglion cells (usually designated "$M_y$" cells) and "x-type" ganglion cells (usually designated "$M_x$" cells). There are significantly fewer $M_y$ cells than $M_x$ cells. Recent work by the present inventors has shown that the $M_y$ cells are responsible for the non-linear component of the optical pathway, while the $M_x$ cells primarily respond in a linear fashion. Of more relevance to the present invention has been the demonstration by the present inventors that the PERG signals measured, with the spatial scales set as they are, display properties (in particular a characteristic phase advance with increasing stimulus contrast) which indicate that these PERG signals are dominated by $M_y$ cells responses rather than any other type of retinal ganglion cell.

Recent work has also indicated that patients having glaucoma also suffer a diffuse, and not just a localised, loss of ganglion cells. In addition, there is data available, from experimental work with primates, to show that the retinal ganglion cells are killed at the onset of glaucoma in proportion to their size (see the paper by Y Glovinsky et al, entitled "Chromic glaucoma damages large optic nerve fibres", which was published in *Investigative Ophthalmology and Visual Science*, Volume 32, page 484, 1991). Furthermore, three separate recent reports of single cell electrophysiological studies all indicate that $M_y$ cells are larger than $M_x$ cells by virtue of their larger receptive field size and more rapid conduction velocities. Those three reports are (i) the paper by E Kaplan and R M Shapley, entitled "X and Y cells in the lateral geniculate nucleus of macaque monkeys", which was published in *Journal of physiology*, Volume 330, page 125, 1982; (ii) the paper by R T Marrocco et al, entitled "Spatial summation and conduction latency classification of cells of the lateral geniculate nucleus of macaques", which was published in *Journal of Neuroscience*, Volume 2, page 1275, 1982; and (iii) the paper by C Blakemore and F Vital-Duran, entitled "Organization and post-natal development of the monkey's lateral geniculate nucleus", which was published in *Journal of Physiology*, Volume 380, page 453, 1986. Since $M_y$ cells are the largest of the retinal ganglion cells, it is a logical conclusion that the $M_y$ cells will be amongst the first cells killed at the onset of glaucoma.

Another factor which makes examination of the $M_y$ Cell function attractive from the point of glaucoma diagnosis is that the coverage factor of $M_y$ cells is very low. This was shown by Crook et al in their paper entitled "Visual resolution of macaque retinal ganglion cells", which was published in *Journal Of Physiology*, Volume 396, page 205, 1988. This factor indicates that the loss of even a single cell will lead to a distinct scotoma in the lattice of $M_y$ cell receptive fields.

A further observation, which makes the frequency-doubled illusion and $M_y$ cells interesting from the perspective of glaucoma diagnosis, is that other neurological disorders which commonly produce visual deficits do not affect vision in this spatio-temporal region, and it is vision in this spatio-temporal region that is necessary for seeing the frequency doubling illusion. For example, amblyopia, Optic neuritis and Parkinson's disease do not appear to affect the patient's perception of rapidly flickered coarse patterns. This conclusion is supported by the information contained in (i) the paper by Hess et al entitled "On the relationship between pattern and movement perception in strabismic amblyopia", which was published in *Vision Research*, Volume 18, page 375, 1978, (iii) the paper by R F Mess and G Plant entitled "The effect of temporal frequency variation on the threshold contrast sensitivity deficits in optic neuritis", which was published in *Journal of Neurology, Neurosurgery and Psychiatry*, Volume 46, page 322, 1983, and also the paper by G K Edgar et al entitled "Optic neuritis, variations in temporal modulation sensitivity with retinal eccentricity", which was published in *Brain*, Volume 113 page 487, 1990, and (iii) the paper by Marx et al entitled "Temporal frequency-dependent VEP changes in Parkinson's disease", which was published in *Vision Research*, Volume 26, page 185, 1986. Thus, stimuli which are designed to produce the frequency-doubled illusion may stimulate a visual pathway that is highly sensitive to glaucomatous damage, and the results of any test for glaucoma which is based on such stimuli are unlikely to be significantly affected by other neurological disorders that modify vision. Indeed, in the specification of Australian patent No 611,585 and in the specification of the corresponding U.S. Pat. No 5,065,767, one of the present inventors has shown that the deficits in the ability of persons to see the frequency doubled illusion are highly correlated with glaucomatous damage.

Further evidence that the frequency doubled illusion arises in the retina rather than at a more central level comes from pattern electroretinogram studies. In several such recent studies, investigators using PERG techniques have adjusted the spatial scale and temporal modulation frequency of their visual stimuli in an attempt to find stimulus conditions which better discriminate between glaucomatous end normal eyes (see, for example, the paper by M A Johnson et al entitled "Pattern-evoked potentials and optic nerve fiber loss in monocular laser-induced glaucoma", which was published in *Investigative Ophthalmology and Visual Science*, Volume 30, page 897, 1989). Although their studies did not encompass the region where the frequency doubled illusion was strongest, these workers have shown that as stimulus conditions approach those required to see the frequency doubled illusion (that is, low spatial frequencies and high temporal frequencies), their ability to discriminate between glaucomatous and normal, healthy eyes was enhanced.

Thus, the present inventors concluded, stimuli which are designed to maximally evoke the frequency doubled illusion from each part of the retina will enhance the value of the electroretinogram signal. If the use of such stimuli is combined with a method which allows independent measurement of the response to these stimuli in each region of the visual field, even better detection of early glaucomatous damage should be possible.

The present inventors then hypothesised that, if this conclusion is correct, (a) a diffuse loss of ganglion cells over the retina will affect $M_y$ cells more than $M_x$ cells in the early stages of glaucoma, so it should be easier to measure a change in the non-linear component of the visual pathway because it will occur at twice the modulation frequency of the stimulus signal, and thus glaucoma sufferers will have a different second harmonic response to intensity modulated patterns from that of persons with normal vision especially if the spatial scale of the stimulus patterns is set by consideration of the areal density of $M_y$ cells, in which case the PERG responses that are recorded will reflect their activity;

(b) the temporal correlate of the spatial frequency doubled illusion described by Kelly would be a frequency doubled temporal modulation of the pattern electroretinogram, provided the stimuli are appropriately scaled (otherwise the responses of inappropriate retinal ganglion cells would dominate the second harmonic response);

(c) the different second harmonic visual response should be exhibited at an early stage of glaucoma, and well before the loss of ganglion cells is sufficient to produce a scotoma; and (d) the different second harmonic visual response should not be exhibited by patients suffering from amblyopia, optic neuritis or Parkinson's disease.

On the basis of this hypothesis, the present inventors devised a method for detecting the occurrence of glaucoma in a subject which involves measuring a parameter that represents the density of the $M_y$ cells and using that measured parameter to construct a number of visual patterns (typically, but not necessarily, grating patterns) which have a spatial distribution that is matched to the spatial distribution of the $M_y$ cells in different zones of the field of view of the human eye. The contrast of these patterns, the distribution and scale of which matches that of the $M_y$ Cells, is then modulated in time and a novel pattern electroretinogram technique is used to measure the second harmonic or frequency doubled response to each spatially matched region. Particular features of the measurement procedure are (a) that the visual patterns or stimuli for the multiple regions in the field of view, and the scale and position of each region, are set to elicit the maximum response from $M_y$ cells at every retinal position, and (b) that the PERG response to each of the regions of the stimulus image is measured at the same time, preferably using a single electrode mounted on the cornea, and that the frequency doubled or second harmonic response from each region is used as the measure of the respective response.

Now a parameter that is believed to be directly related to the angular separation of ganglion cells is the critical frequency at which the phenomenon known as "aliasing" or "spatial aliasing" occurs. Spatial aliasing can manifest itself as an apparent reversal of the direction in which a grating pattern is drifted across the visual field of a subject. This optical illusion arises when the density of an array of samplers is insufficient to reconstruct the highest spatial frequency detected by an individual sampler. Strictly speaking, a two dimensional array of samplers will be able to provide veridical information about an input frequency up to a spatial frequency which is exactly equal to half the frequency defined by the coarsest or widest separated rows of nearest neighbour detectors in the sampling lattice, which in this case is the lattice of $M_y$ cells. This critical sampling limit is often called the Nyquist frequency, although it is more aptly termed the "critical spatial frequency". It is represented in this specification by the symbol $S_c$.

If $M_y$ cells constitute only 1 per cent of all ganglion cells, then they must alias because the highest spatial frequency to which the individual cells can respond is about 6 to 8 times higher than the Nyquist frequency necessarily imposed by their low areal density. Under these circumstances, a variety of effects should occur. One of the most interesting of these effects is that a moving sinusoidal intensity grating pattern which has a spatial frequency that is above the cut-off frequency of the sampling array (but less than twice the sampling frequency) will be seen as a lower spatial frequency pattern moving in a different direction. For a one-dimensional array of sampling elements, the aliased pattern will always drift in the opposite direction.

For a two-dimensional array of sampling elements, the direction of motion will appear to be opposite to actual motion only near the cut-off frequency. The exact interpretation of $S_c$ vis-a-vis the underlying density of the aliasing units depends upon the geometry of the packing of the units or cells in question. The two cases of usual interest are square lattices of sampling units and hexagonal lattices of sampling units. However, it can be shown that a hexagonal sampling lattice with the same density of samplers achieves about 1.075 times higher than a square lattice (see the paper by R M Merserseau, entitled "The processing of hexagonally sampled two-dimensional signals", which was published in *Proceedings of the Institute of Electrical and Electronic Engineers*, Volume 67, page 930, 1979). Clearly, the effect of the sampling lattice geometry is quite small.

If the frequency doubled percept described above is due to the $M_y$ retinal ganglion cells, then values of $S_c$ obtained from experiments using the frequency doubled stimulus wall be direct measures of the areal density of the ganglion cell population within the region of the retina tested. In the glaucomatous retina, one can make two predictions about the measured values of $S_c$. If the $M_y$ cell losses have occurred at random positions across the retina, the value of $S_c$ should remain fixed but the variance about the measured value of $S_c$ should increase. Alternately, if the cell losses are correlated in some way (for example, if on or off $M_y$ cells have been selectively damaged), then $S_c$ should shift to lower spatial frequencies or the certainty of $S_c$ would be reduced by random disorder injected into the lattice by neurone death. In principle, this information could be used to assess glaucomatous damage. Obtaining this information and assessing it to discover such variance or shift or reduction of certainty of $S_c$ constitutes a separate aspect of the present invention. However, in the form of the present invention which uses pattern electroretinogram measurements, as described earlier in this specification, the measurements of $S_c$ are used to specify the spatial scale of visual stimuli presented in the zones of the visual field to match the local density of $M_y$ cells in corresponding patches of the retina. A combination of these two methods is also possible. In such a combination, the spatial grain and/or the regularity of the $M_y$ cell array is assessed using an electroretinogram recording of retinal responses to drifting frequency-doubled gratings of varied spatial frequencies, by determining the extent of aliasing. In addition, the direction of travel of the aliased image is noted, from observation of the temporal phase of the recorded signals.

As noted above, the present invention requires the establishment of independent visual stimuli, each of which is used in connection with a respective one of a number of regions or zones in the visual field in the generation of a pattern electroretinogram. The size of these regions and the internal structure of these regions are set to be optimal for the $M_y$ cells using information obtained from aliasing observations. A novel measurement scheme, which permits neural (electrical) responses to each of these stimulus regions to be assessed, preferably at the same time and with a single measurement electrode, is then adopted. To measure pattern electroretinogram responses from each retinal region in parallel, that is to say at the same time while using only one electrode on the eye, rapid data processing and optimal mathematical characteristics are achieved by requiring the functions which describe the temporal modulation of the contrast of adjacent regions of the visual stimulus to be orthogonal. The stimuli temporal modulation functions for each stimulus region should also have the property that responses due to higher order interactions between stimulus regions should also be distinct from the second harmonic response of the pattern electroretinogram (PERG), which is taken to be the temporal correlate of the frequency doubled illusion, provided the spatial scale of the stimulus pattern is designed to match that of the $M_y$ cells.

Details of some of the work undertaken to verify the present inventors' hypothesis and demonstrate the efficacy of the present invention will now be described with reference to the accompanying drawings.

DETAILED DESCRIPTION OF IMPLEMENTATION OF THE PRESENT INVENTION

The Critical (Nyquist) frequency was measured for a number of subjects, some of which had normal vision and some of which were suspected of suffering from glaucoma. These data were used to set the spatial scale of the PERG patterns.

In the aliasing experiments, which were conducted to determine the Nyquist frequency, sinusoidal grating patterns were produced, using computerised image-generating techniques, on the screen of a Joyce Electronics cathode ray tube with a (P4) phosphor adjusted to a mean luminance of 297 cd $m^{-2}$ and having a frame refresh rate of 100 Hz. The grating patterns were viewed through apertures cut in a mask. A few rectangular apertures were used but most experiments involved circular apertures with angular diameters ranging between 1 and 23.6 degrees. Most of the experiments were done with circular apertures having diameters less than 4°. With a few exceptions, the modulation frequency of the grating patterns for the aliasing experiments was 20 Hz and the sinusoidal grating patterns were usually drifted to produce an associated temporal frequency of 1 Hz. However, experiments with other drift frequencies between 0.5 Hz and 4.0 Hz were also conducted. These parameters are in good agreement with those described elsewhere for producing the frequency doubled illusion.

The basic experimental paradigm involved each subject guessing the direction of drift of grating patterns, the contrast of which was modulated at high rates. Subjects signalled their desire to see a new grating pattern by pressing a lever. A tone accompanied the presentation of a new grating pattern. Grating patterns were presented for 2 seconds after which time their contrast was reduced to zero. Subjects could register their opinion of the drift direction of the pattern before the end of the 2 seconds period, in which case a new grating pattern was presented after a hundred milliseconds. After or during the 2 seconds presentation time, the subject had the option of having the same grating presented again, but the direction of drift was randomised for each presentation so that multiple presentations conveyed no information about the direction in a subsequent trial. Typically, nine spatial frequencies were used in each experiment. After the presentation of a set of nine grating patterns, the presentation order was randomised and 30 repetitions of each grating pattern were typically presented. In many cases, the experiments were repeated after periods varying from 1 day to 30 days. The reproducibility of results was found to be very good over these periods.

Figure 1:
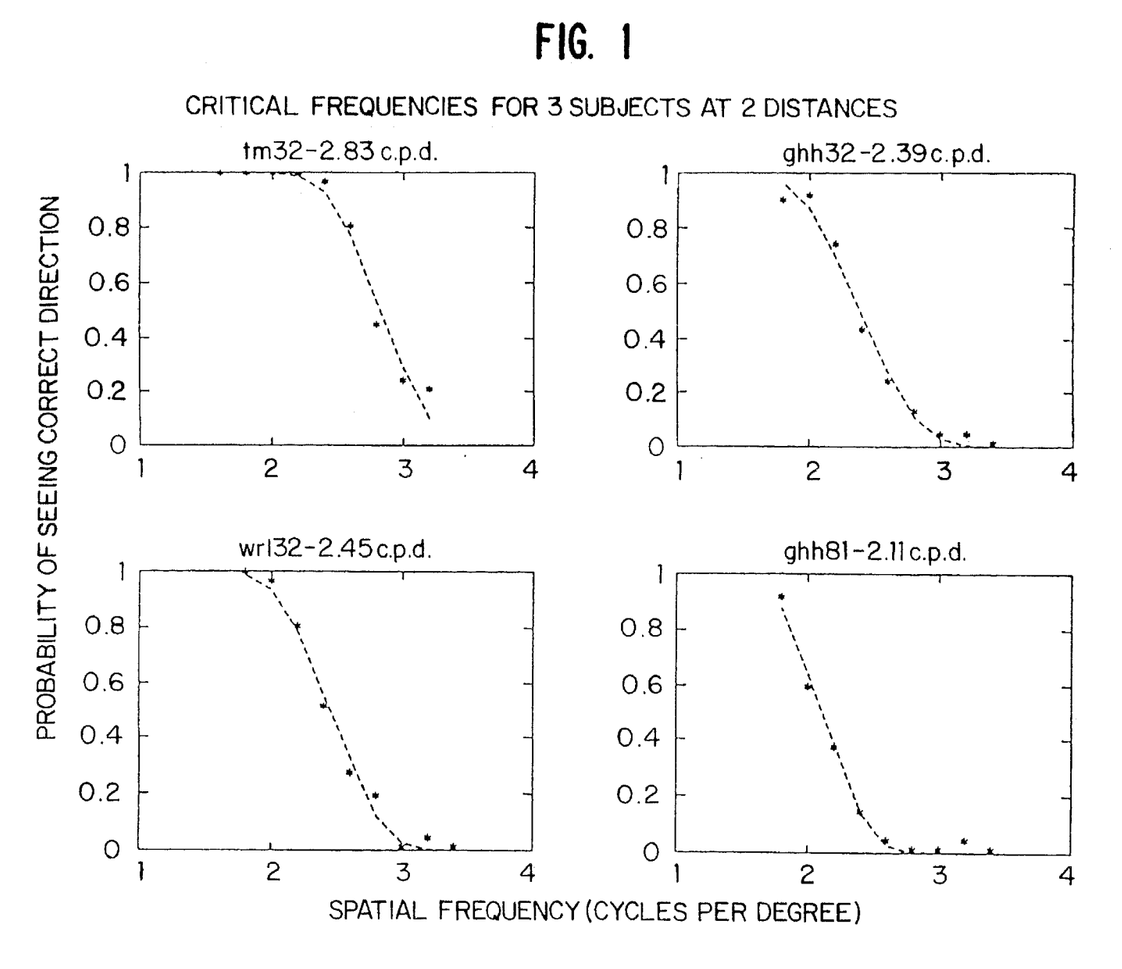
FIG. 1 is a graphical representation of the results of four experts which were performed to determine the Nyquist frequencies of three subjects.

The data obtained from the aliasing experiments took the form of sigmoidal curves expressing the probability of the subject seeing the correct direction of drift as a function of spatial frequency. A selection of such curves for three subjects (each subject is identified by the initial letters of the subject's name and the age in years of the subject) are shown in FIG. 1. Each ordinate shows the probability of seeing the correct direction of drift of a set of frequency doubled grating patterns. A probability of 0 indicates that a subject consistently sees the incorrect direction. The spatial critical frequency or Nyquist frequency, $S_c$, was taken as the frequency at P=0.5, which corresponded generally to the point of inflection of each curve. The slope at P=0.5 shows the variance of $S_c$.

Predictably, the performance of subjects at the critical frequency was found to be completely random. At spatial frequencies below $S_c$, each subject becomes progressively more accurate (complete accuracy is when P=1.0). At frequencies above $S_c$, each subject becomes more inaccurate, and is completely incorrect when P=0. The most obvious feature of these tests is that the subjects clearly experienced a reversal of the perceived motion of the grating pattern, and that above a critical spatial frequency of the patterns, ability to guess the correct direction of motion of the pattern went to near 0 probability. Also clear is that the assumptions behind the curve fitting model—fits to 1 minus the normal probability density function (the dashed lines in FIG. 1)—appear to be justified.

Before attempting to assess $S_c$ as a function of retinal eccentricity, several types of control experiments were conducted to check that the motion reversal effect associated with the frequency doubled grating patterns was indeed indicative of aliasing. In the first set of controls, four viewing distances were used: 40.6 cm, 81.3 cm, 163 cm and 325 cm. These four octaves of viewing distance were used in part to provide controls to show that spatial frequency, and not the number of cycles displayed on the screen of the cathode ray tube, was the critical factor in producing the illusory reversal of drift direction. The phenomenon of drift direction reversal as a function of spatial frequency was observed at all of these viewing distances. The measured value of $S_c$ was also found to be independent of drift rate over the three octaves of drift frequency tested (0.5 Hz, 1.0 Hz and 2 Hz). The critical frequency, $S_c$, was also little affected by grating orientation, or by contrast.

The results of all of these tests taken together strongly indicate that the motion reversal effect is strictly a function of spatial frequency and therefore is most likely to be due to aliasing. These and other experiments showed that it is reasonable to associate the measured values of the critical frequency, $S_c$, with the density of ganglion cells of the subject.

Figure 2:
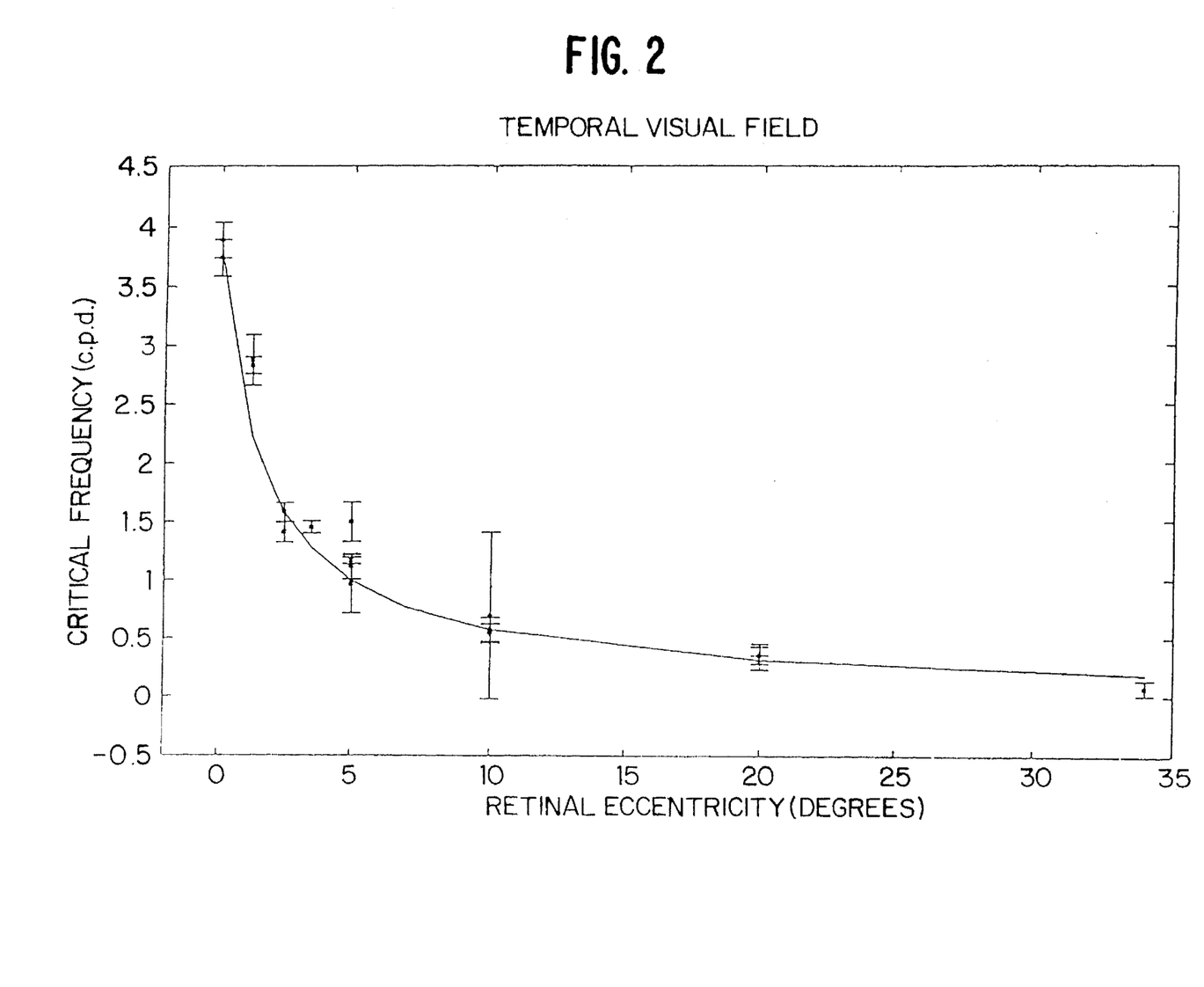
FIG. 2 is a plot of the variation of the Nyquist frequency with retinal eccentricity for one subject for his nasal visual field.

In some of the experiments where $S_c$ was assessed at large angles of retinal eccentricity, the subjects were asked to fixate a light emitting diode, the brightness of which was subjectively the same as that of the activated phosphor on the screen of the cathode ray tube. The diode was displayed at a distance which was as nearly as was technically possible to the same viewing distance as the c.r.t. screen. Grating patterns were viewed through circular apertures and, at each eccentricity, the aperture size was adjusted to be the smallest aperture in which a practised subject could still reliably perform the psychophysical test. The results of these experiments for the temporal visual field of the subject "tlm" are shown in FIG. 2. Predicted values of $S_c$ as a function of eccentricity, $S_c(ecc)$, were found to be directly related to cell areal density, D(ecc), according to the relationship:

$$S_c(ecc)=(D(ecc)/2\sqrt{3})^{1/2}. \qquad (1)$$

It should be noted that the values of $S_c(ecc)$ obtained from Equation (1) assume a hexagonal packing of $M_y$ cells and are 1.07457 times higher than one would expect for square packed cells with the same local densities. This small change in predicted density does not significantly alter the findings reported below.

Anatomical data from a paper by M Connolly and D Van Essen entitled "The representation of the visual field in parvicellular and magnocellular layers of the lateral geniculate nucleus", (which was published in *Journal of Comparative Neurology*, Volume 226, page 544, 1984), was used in conjunction with Equation (1) to determine if $S_c(ecc)$ could reasonably be determined by the known anatomical cell densities. At the anatomical level, $M_y$ cells and $M_x$ cells cannot yet be distinguished. Electrophysiological recordings from single units by a variety of authorities, however, indicate that $M_y$ cells should be about 10 per cent of all M cells. The solid line in FIG. 2 is a fit based on the data of Connolly and Van Essen, based on the parsimonious assumption that 10 per cent of M cells are $M_y$ cells at every eccentricity. Clearly the anatomical and $S_c(ecc)$ data are in good agreement, indicating strongly that the source of the frequency doubled illusion is the $M_y$ cells and the visual stimuli based on this scaling would be optimal for stimulating the $m_y$ cells at every retinal eccentricity. The actual function describing the solid curve in FIG. 2 is:

$$D(ecc)=176(1.75+ecc)^{-1.99}. \qquad (2)$$

It will be noted by persons skilled in this field that the value of 176 in Equation (2) is approximately $\frac{1}{20}$th the figure quoted by Connolly and Van Essen for the central density (cells per degree$^2$) of all M cells in the retina, indicating that Equation (2) takes into account one hemifield only and that the $M_y$ cell density is taken as $\frac{1}{10}$ of the total M cell pathway. In general, it can be said that good fits to the $S_c(ecc)$ data can be obtained using Equation (2) and making the assumption that the units involved have a density which is 10 per cent of that for all M cells. Although slight modifications to the parameters used by Connolly and Van Essen were required, all the modifications brought the model parameters examined here closer to the values found by those authors for the P ganglion cells. Thus it may be concluded that the density of units subserving the frequency doubled illusion reported by Kelly is a good match to the probable density of $M_y$ cells and that, at least in humans, the density of these cells is close to a scalar multiple of the density of both the M and the P retinal ganglion cells.

Having obtained the information on the projected density into visual space of what appears to be the $M_y$ cells, the present inventors then divided the visual field into nine regions or zones and constructed individual visual stimuli for each of those nine regions. The size of the regions and the spatial frequencies presented in each region were scaled according to the measured values of $S_c(ecc)$.

Figure 5:
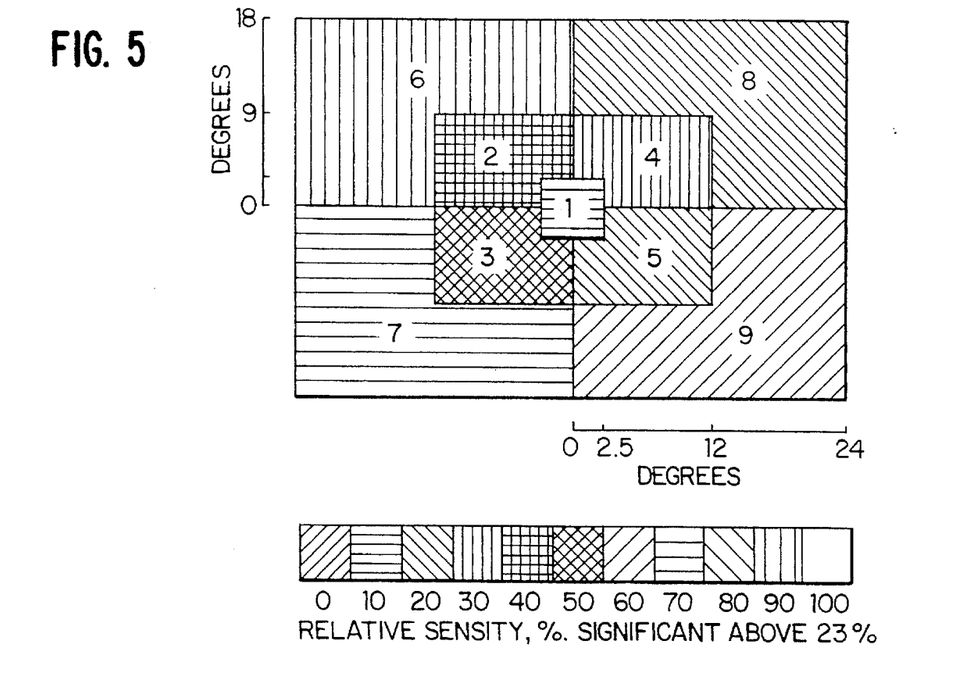
FIG. 5 shows the regions of the field of view selected for PERG measurements, and the relative sensitivities of one subject to the visual stimuli used for the PERG evaluation. The variations in the responses to the visual stimuli show that the subject has glaucoma.

The size of the regions is graphically represented in FIG. 5. The main features of these regions are (a) that they split the visual field into four quadrants, and (b) that within each quadrant are regions that scale upward in size with increasing eccentricity according to a scalar multiple of the determined values of $S_c(ecc)$. This geometry and segmentation of the visual field thus attempts to capture the main features of glaucomatous field losses, which include (i) differential field losses in the superior and inferior visual field, particularly in the nasal visual field, and (ii) nasal and temporal hemifield defects, such as clear hemianopia or temporal sectoral defects. The radial scaling of region size was designed to provide optimal stimulation of the retinal regions corresponding to the stimulus regions. In the experiments conducted by the present inventors; each region was filled with spatial frequencies which, at the centre of each region, were half the value of $S_c(ecc)$ at that eccentricity. Since glaucomatous scotomas often assume an arc-like appearance, it would be advisable to make the regions elliptically symmetric, but this was not considered to be essential for the demonstration of the efficacy of the present invention.

Having selected a series of visual stimulus patterns for the retinal regions (the patterns were all grating patterns, but it should be apparent to persons skilled in this field that other types of patterns may be used), pattern electroretinogram measurements were then conducted with the subject. The visual stimuli signals were presented on a Barco 7551 colour monitor, the colour temperature of which was calibrated to 5900° K., and the frame rate of which was 100 Hz. This frame rate is about four times the highest stimulus frequency, and is thus about the minimum rate of presentation of data. However, any frequency which is above the Nyquist rate of the desired contrast modulation frequencies can be used as the presentation rate. As in the aliasing experiments, the response of the cathode ray tube screen was linear up to contrasts of at least 80 per cent. At contrasts greater than 80 per cent, the distortion was up to a few per cent. Experiments using a photodiode demonstrated that no significant second harmonic components arose from the cathode ray tubes.

In the pattern electroretinogram (PERG) experiments, to achieve orthogonal stimuli in each visual region, the contrast of each region was modulated with one of nine different temporal frequencies in a narrow band of frequencies in the range of from 22 Hz to 24 Hz. In principle, any band of frequencies in the range of from 10 Hz to 45 Hz could be used to modulate the contrast of each region, since these frequencies have been shown to be where the frequency doubled illusion is visible.

In all the PERG experiments, a conventional corneal electrode was used. However, any suitable electrode arrangement may be adopted when implementing the present invention. It should also be noted that, in clinical implementations of the present invention, it may be advisable with some subjects (namely those who experience difficulty in fixating a central point in the field of view) to monitor the eye movement during the PERG measurements. A conventional electro-oculogram may be used for this purpose. The PERG data will then be modified according to the degree of eye movement of the subject.

Figure 4:
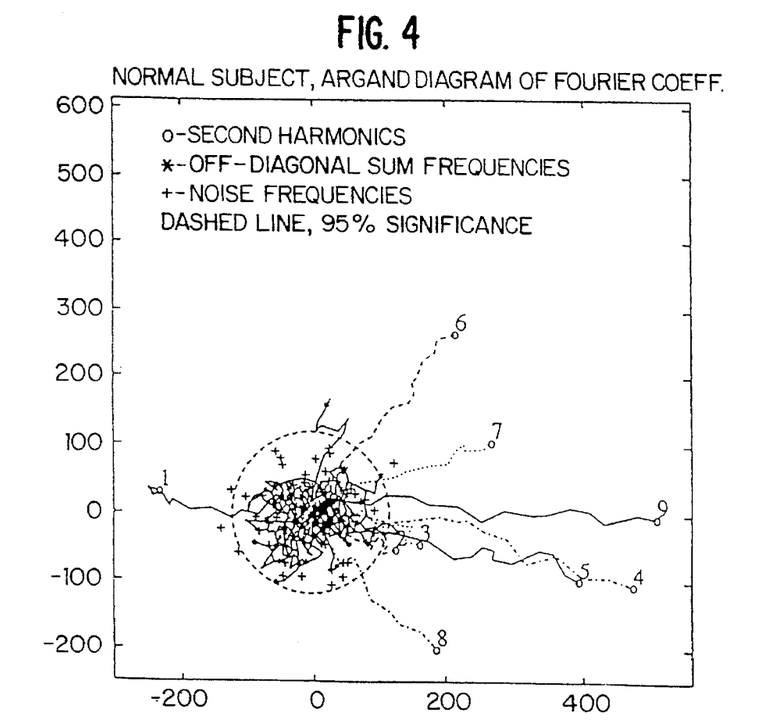
FIG. 4 is an Argand diagram of data presented in FIG. 3.
Figure 7:
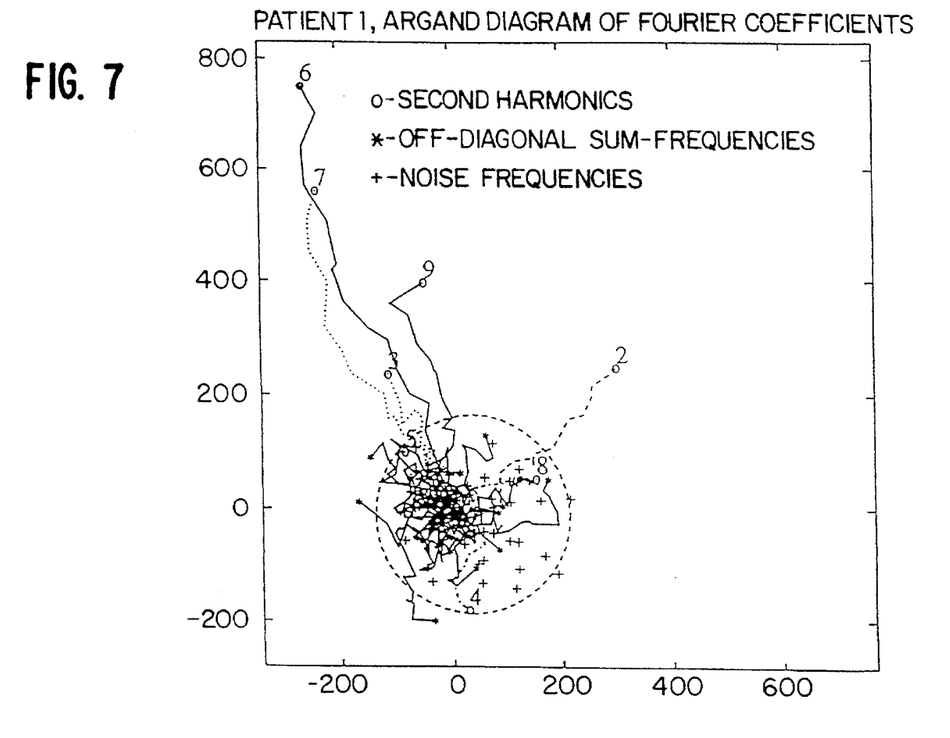
FIG. 7 is an Argand diagram of the Fourier coefficients of the data shown in FIG. 5.

Since the temporal correlate of the spatial frequency doubled illusion is a frequency doubled temporal response, provided the spatial scale of the stimulus pattern is designed to match that of the $M_y$ cells, the present inventors examined the strength of the response signal from each region at the second harmonic of each stimulus frequency. However, to avoid distortion frequencies, arising from second order interactions the simultaneously presented between stimulus regions, being added to or subtracted from the frequency doubled response modulation, it was necessary to choose frequencies such that all possible pair-wise sums were distinct from the second harmonics of the input frequencies. Frequency resolution was set by the length of each PERG stimulus run. Run length was set to 8192 video frames or 40.96 seconds. Responses were then analysed by a fast Fourier transform technique with a resulting frequency resolution of $1/40.96=0.0244$ Hz. The response signals obtained from several runs of 40.96 seconds were then averaged and the accumulated averages of the frequency doubled components were displayed on plots of the relevant Fourier coefficients on the complex plane (for example, as shown in FIGS. 4 and 7). These plots are usually termed "Argand diagrams". In an Argand diagram, the contribution of each repetition to the final averaged coefficients can be seen as a vector in the complex plane, showing both amplitude and phase.

The actual significance of the frequency component of a response signal is related to its amplitude, which is the modulus of the Fourier transform coefficient at that frequency, $A(f)$. A test of significance for a particular frequency can be done as follows. Under a null hypothesis of no signal, the real and imaginary parts of the Fourier Transform coefficients, Real $(A(f))$ and $Imag(A(f))$, are independent normal variates with zero mean and some variance $\sigma^2$. The squared modulus of the coefficient, $|A(f)|^2$, is then $\sigma^2$ times a chi squared variate on 2 degrees of freedom. An estimate $s^2$ of $\sigma^2$ is obtained from frequencies not in the set of second order stimulus frequencies, say with n degrees of freedom. An F-test is then done on the quotient $|A(f)|^2/s^2$, with $(2,n)$ degrees of freedom. The test can be graphically represented in a clear way since significance of a frequency component occurs if, and only if, the coefficient $A(f)$ lies outside the dashed circle shown on the Argand diagrams of FIGS. 4 and 7.

During both the aliasing and the PERG experiments, all of the subjects being examined held their heads against a standard ophthalmic head rest. In the PERG experiments, standard recording techniques were used, the novel features being the geometry of the visual stimuli and the fact that the PERG frequency components at the second harmonic of the stimulus frequencies were used as the measure of response.

Figure 3:
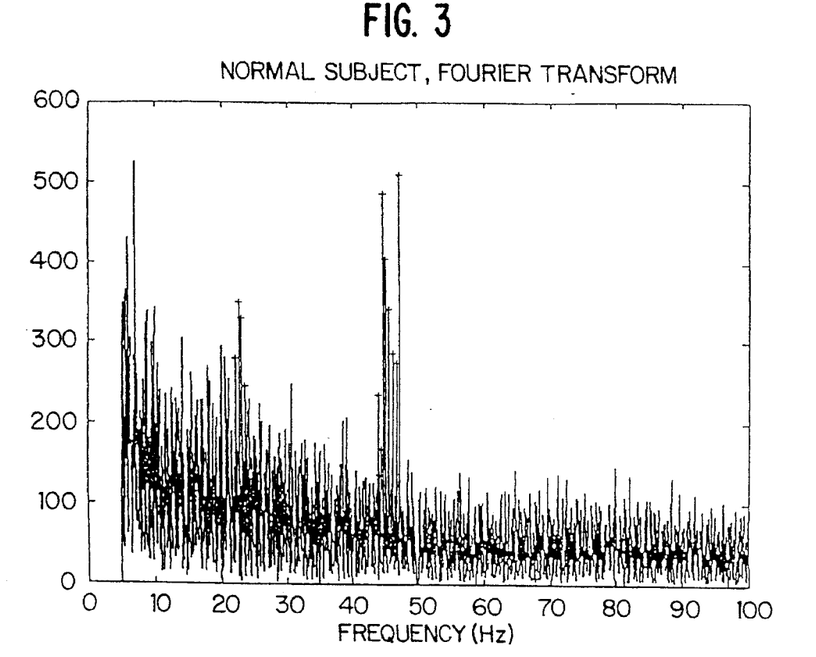
FIG. 3 shows the variation with frequency of the strength of the Fourier components of the eye of a subject with normal vision.

FIG. 3 demonstrates the strength of the Fourier components from each eye region in a normal subject, the second harmonics of the stimulus frequencies being the cluster of peaks in the band 44 to 46 Hz. The significance of these frequency components can be seen in FIG. 4, where the frequencies are represented as vectors in an Argand diagram. The numbers at the head of each vector in FIG. 4 correspond to the stimulus regions evoking the responses. The slightly tortuous path of each frequency represents the path across the complex plane that the individual Fourier coefficients took in the course of the sixteen averages. Thus, unlike the centrally clustered noise frequencies, the frequency components from each stimulus region are highly significant, being well beyond the dashed circle in FIG. 4 which represents significance at the $p=0.05$ level.

FIG. 5, in addition to showing the nine regions of the visual field selected by the present inventors, illustrates the data obtained from a subject suffering from glaucoma. The results shown are each the average of sixteen experiments each of 40.96 seconds duration. The strength of the PERG signal from each region of stimulus is graphically demonstrated in FIG. 5, where the rectangular regions represent the actual size and distribution of our nine stimulus regions. The grey-scale bar at the bottom of FIG. 5 indicates that the stimulus regions having a grey level which is greater than 23 per cent were significant. Thus, FIG. 4a represents a diagram of the relative sensitivities of different part of the subject's visual field.

Figure 6:
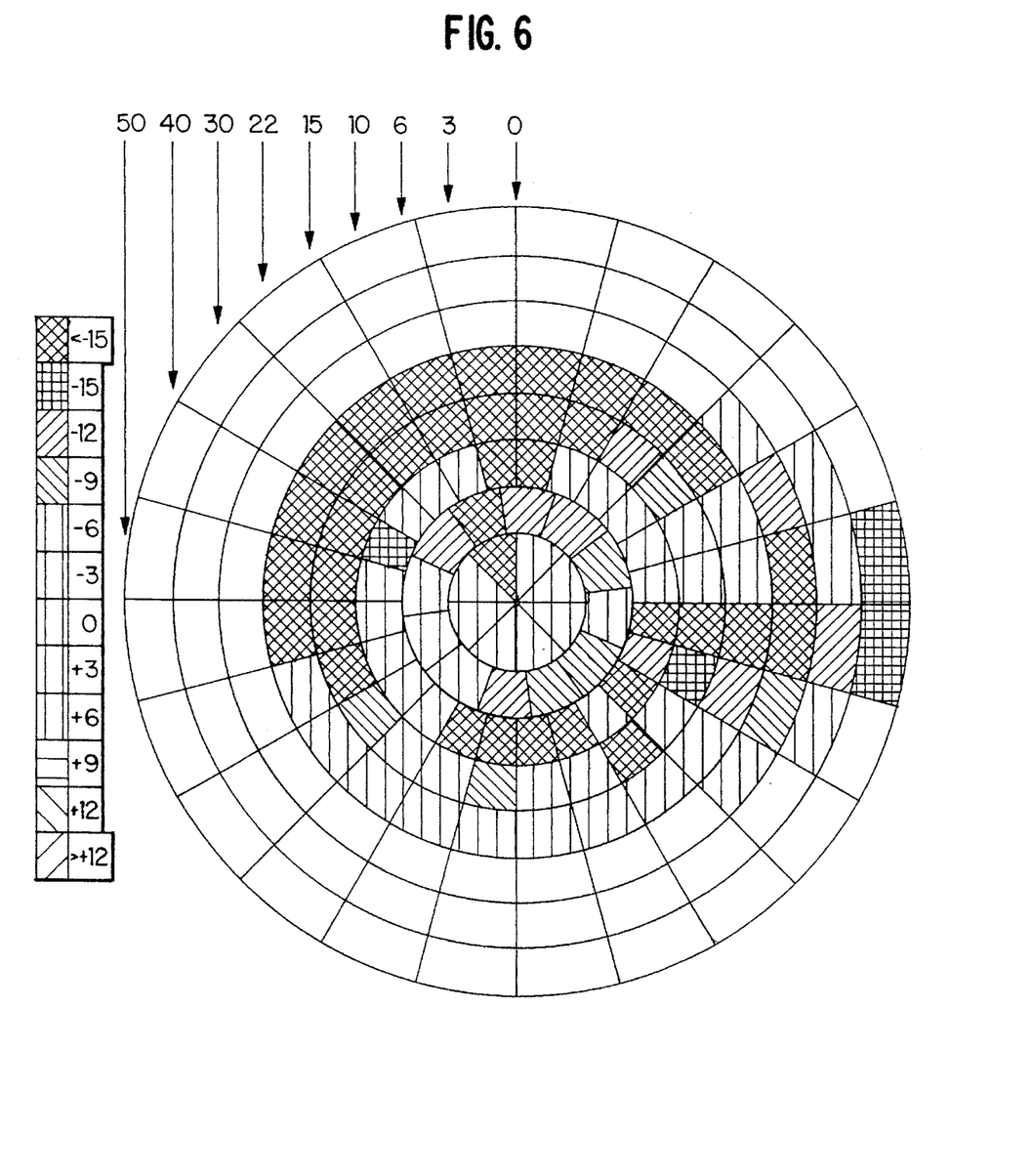
FIG. 6 is a presentation of the data obtained, from the same subject who provided the data for FIG. 5, with a conventional "Opticon" perimetry examination.
Figure 8:
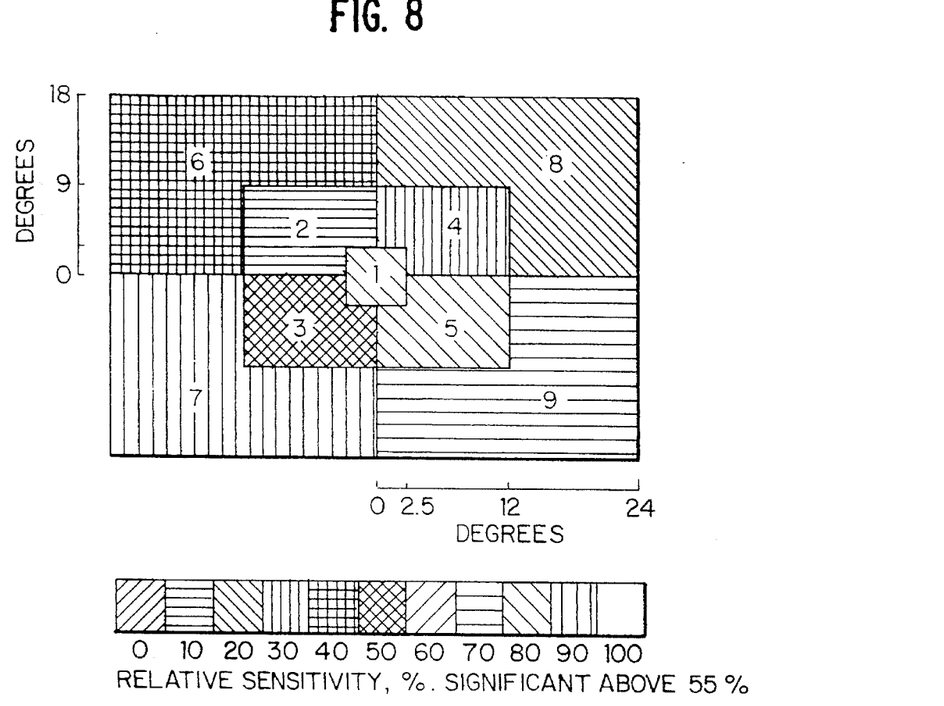
FIG. 8 presents the same data as that shown in FIG. 5, obtained from another subject with glaucoma.
Figure 9:
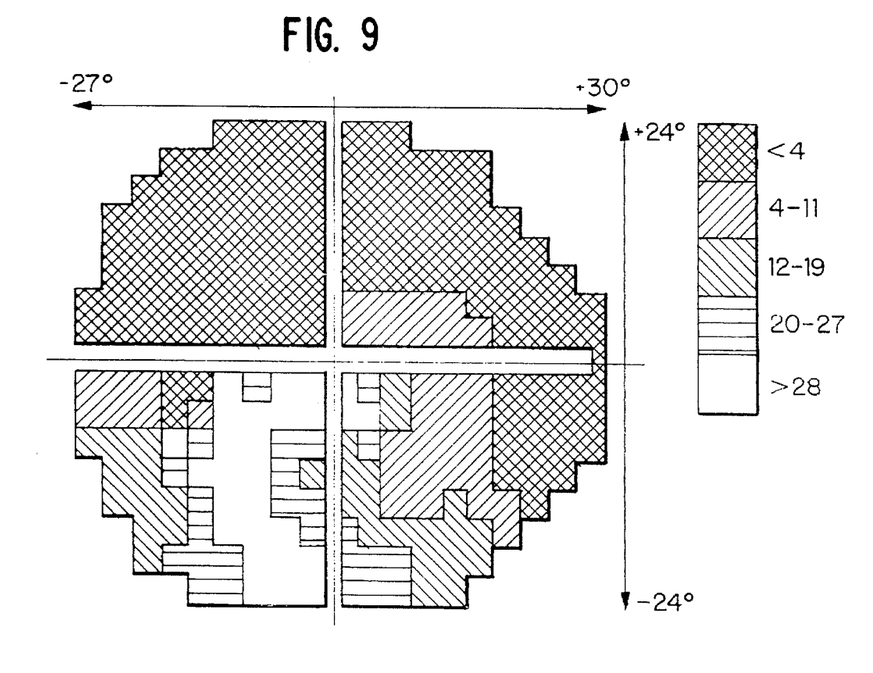
FIG. 9 is a presentation of data obtained, from the same subject who provided the data shown in FIG. 8, using the conventional "Humphrey" method of retinal examination.

FIG. 6 shows the results of a more conventional "Opticon" perimetery examination of the same eye. It will be seen that there is rough agreement between the two methods (note that the radial scale in FIG. 6 is logarithmic and so it is difficult to visually compare the data in FIG. 6 with the date presented in FIG. 5). The major difference between the two results of the two examinations of the subject is the visual field region corresponding to region 6 of FIG. 5. The present inventors cannot account for this discrepancy, particularly because the signal from region 6 was extremely significant (see FIG. 7, which is the Argand diagram for the same subject). Possibly the two methods are measuring different effects. Much better agreement was found between the data obtained for another subject using the present invention (FIG. 8) and the perimetry data obtained for the same subject using the "Humphrey" (program 24/2) method, which is presented as FIG. 9. FIGS. 8 and 9 are drawn to the same scale. It will be noted that the data for every region except region 3 of FIG. 8 is in good agreement with that obtained using the standard ("Humphrey") perimetry analysis technique.

It will be apparent that a comparison of the responses from the various regions of the visual field, presented in FIGS. 5 and 8, demonstrates (i) a variance in the $M_y$ cell density of each subject and thus (ii) that each of those subjects is suffering from glaucoma. The need for sixteen repeats in the PERG experiments described above was primarily because the electronic equipment used by the present inventors was less than optimal. It was expected that with improvements in the signal detection analysis technique, the number of stimulus regions could be increased and the number of averages required could be reduced to four or less. It was also expected that improved equipment would permit an assessment of the two eyes of a subject to be performed at the same time, and at a wider range of visual eccentricities than is practically allowed by the time constraints of conventional perimetry.

Accordingly, the present inventors conducted a study of 86 other persons, in which the PERG method of the present invention and the Humphrey perimetry technique were both used, and the data obtained by the two techniques were quantitatively compared. Improved recording methods were used in this second study. The 86 subjects were classified into four groups: (1) normals, (2) persons weakly suspected of having glaucoma, (3) strong suspects and (4) persons suffering from glaucoma. Only the glaucoma subjects showed scotomas with the Humphrey perimetry technique. Each strong suspect had other glaucoma symptoms, such as elevated intraocular tension, and also had an observed change in his or her optic disc (determined from repeated photographic records of the optic disc). Weak suspects had no observed change in their optic discs. Only the right eyes of the subjects were used in this study. The "24-2" program of the Humphrey Perimeter technique was used to obtain standard perimetric visual field threshold data from all 86 subjects in the study group. With the improved recording equipment, spatial resolution of the data obtained with the Humphrey perimeter technique was significantly finer than in the previous experiments. This data was used to produce a map of predicted values for each of the nine image regions or "zones" covered by the PERG stimulus. These predicted amplitudes, derived from the perimetry data, were then compared with the data obtained with the PERG method. If the two data should be in good agreement, this would indicate that the PERG method, while being quicker and potentially more objective, was at least as good as the perimetry method in detecting glaucomatous visual field losses.

Regression analysis of the resultant data using "Student's t-test", to obtain "t" and "p" values for the subjects, showed that, in general, the correlation between the two sets of data was very good, with the exception of the data obtained from the strong suspects group. The poor performance of the strong suspects group appears to arise from the initial period of the experiment, when the operator was unfamiliar with the equipment. If data is selected on the basis of the number of PERG zone amplitudes which are significant (see FIG. 7), the significance of the correlation increases. For example, choosing PERG data with three or more significant zone-amplitudes showed that 74.6% of these data have p values of 0.1 or less. If the sample is further restricted to PERG data sets with six or more significant zone amplitudes, the proportion with $p<0.1$ rises to 85.7%. Strictly speaking, for positive correlations, "t" is a monotonically increasing non-linear function or correlation. As there are 7 degrees of freedom in all cases examined by the present inventors, the "p" values are also related to the degree of correlation.

Again, it was clear that further averaging or improved recording techniques would improve the correlation. Better recording seems the most likely avenue for enhancement of the PERG method, for amongst the 21 data sets with 7 or more significant ($p<0.05$) PERG zone amplitudes in this study, the mean number of averages taken was $3.9\pm1.20$ sd, so the good results in the data set are due mainly to good recordings, rather than more extensive averaging.

Thus, it will be seen that the present invention, in providing simultaneous assessment of multiple regions of the visual field of a subject, with respective visual stimuli tailored to the geometry of the regions and to the density of cells with high sensitivity to retinal damage, provides a rapid, objective and sensitive assessment of damage to the eye by glaucoma.

Those skilled in this field will appreciate that the exemplary embodiments of the present invention that have been described above may be modified or varied without departing from the present inventive concept. For example, the number of zones in the visual field of a subject may be other than nine. Indeed, in a new set of PERG experiments, it is proposed to use 32 zones in the visual field.

We claim:

1. A method of assessing the presence of glaucomatous damage to the visual system of a subject, the method comprising the steps of:

(a) dividing the visual field of view of the subject into a number of zones of a pattern electroretinogram stimulus;

(b) generating, using data about the areal density of retinal ganglion cells on the retina of the human eye, such data being obtained from determinations of the critical spatial frequency (Nyquist frequency) of persons with normal vision, a set of visual stimulus signals which, on the basis of the measured areal density of receptors, should elicit an electroretinogram response from the subject which is dominated by the activity of $M_y$ ganglion cells of the subject;

(c) simultaneously, presenting the visual stimuli to the eve of the subject while the subject observes the pattern electroretinogram stimuli by fixating on the center of said pattern electroretinogram stimulus, and obtaining a response signal which, by virtue of the temporal modulation of the stimuli applied to each zone being linearly independent, and such that pairwise sums of input frequencies are different from second harmonics of the input frequencies, can be decomposed into components by a process such as linear regression, each component relating to a respective one of the zones;

(d) comparing the electroretinogram response amplitudes and phases for the zones and the expected response components for the zones, and noting any significant difference between the observed and the expected response amplitude and phase of any zone of the visual field, any such difference indicating a change in the $M_y$ cell function in that zone, which is attributable to the effect of glaucoma on the subject.

2. A method as defined in claim 1, in which the visual stimulus signals applied to said zones are patterns having spatial scales based on the critical spatial frequency for observing motion reversal of moving frequency doubled sinusoidal grating patterns.

3. A method as defined in claim 2, in which said visual stimulus signals applied to the zones are effected by modulating the contrast of each zone with a different respective temporal frequency in the range of from 10 Hz to 45 Hz.

4. A method as defined in claim 1, in which said visual stimulus signals applied to the zones are effected by modulating the contrast of each zone with a different respective temporal frequency in the range of from 10 Hz to 45 Hz.

5. A method as defined in claim 4, in which each temporal frequency is in the range of from 22 Hz to 24 Hz.

6. A method as defined in claim 4, including the additional steps of (i) varying the spatial phase of the sinusoidal grating patterns with time to produce a translation of the grating patterns, and (ii) observing the temporal phase of the resulting PERG data in a manner such that spatial aliasing effects analogous to those observed in the assessment of the critical spatial frequency for motion reversal are electronically quantified, thus providing information about the spatial granularity and regularity of the $M_y$ cells of the region of the retina viewing each zone.

7. A method as defined in claim 1, in which, for the period during which the visual stimuli signals are applied to said zones, an electro-oculogram of the subject is obtained, to enable modification of the electroretinogram response components in accordance with eye movements of the subject.

8. A method as defined in claim 1 in which each of the stimulus signals applied to each zone is orthogonal in time to the visual signals applied to all other zones, such that the decomposition of the response into components is computed by Fourier transforms.

* * * * *